(12) United States Patent
Watkins et al.

(10) Patent No.: US 7,321,108 B2
(45) Date of Patent: Jan. 22, 2008

(54) DYNAMIC FOCUSING METHOD AND APPARATUS

(75) Inventors: Cory Watkins, Eden Prairie, MN (US); Mark Harless, Plymouth, MN (US); David Vaughnn, Edina, MN (US); Pat Simpkins, Edina, MN (US); Shaileshkumar Goyal, Rajasthan (IN); Gerald Brown, Plano, TX (US); Brian Delsey, Frisco, TX (US)

(73) Assignee: Rudolph Technology, Inc., Flanders, NJ (US)

( * ) Notice: Subject to any disclaimer, the term of this patent is extended or adjusted under 35 U.S.C. 154(b) by 0 days.

(21) Appl. No.: 11/625,640

(22) Filed: Jan. 22, 2007

(65) Prior Publication Data

US 2007/0114358 A1    May 24, 2007

Related U.S. Application Data

(60) Division of application No. 11/179,047, filed on Jul. 11, 2005, now Pat. No. 7,196,300, and a continuation-in-part of application No. 10/622,848, filed on Jul. 18, 2003, now Pat. No. 7,170,075.

(60) Provisional application No. 60/587,570, filed on Jul. 12, 2004, provisional application No. 60/587,302, filed on Jul. 12, 2004, provisional application No. 60/587,216, filed on Jul. 12, 2004.

(51) Int. Cl.
*G02B 7/04* (2006.01)
*G02B 27/40* (2006.01)
*G02B 21/36* (2006.01)
*G01N 21/00* (2006.01)

(52) U.S. Cl. .............. 250/201.2; 250/201.3; 250/201.4; 250/559.05; 250/559.07; 250/559.08; 250/559.29; 356/601; 356/609; 356/614; 356/624; 359/368; 359/379; 359/380; 359/678; 359/694; 359/698; 359/823; 359/432

(58) Field of Classification Search .. 250/201.2–201.4, 250/559.05, 559.07, 559.08, 559.29; 356/609, 356/601, 614, 624; 359/368, 379–384, 678, 359/694, 698, 823, 432
See application file for complete search history.

(56) References Cited

U.S. PATENT DOCUMENTS

| | | |
|---|---|---|
| 5,647,025 A | 7/1997 | Frost et al. |
| 5,780,866 A | 7/1998 | Yamamura et al. |
| 5,864,056 A | 1/1999 | Bell et al. |
| 6,052,223 A * | 4/2000 | Yoneyama et al. ......... 359/381 |

(Continued)

*Primary Examiner*—Davienne Monbleau
(74) *Attorney, Agent, or Firm*—Dicke, Billig & Czaja PLLC (57) ABSTRACT

A method and apparatus for dynamically focusing an imaging mechanism on a moving target surface having a variable geometry is herein disclosed. Apparatus for focusing an imaging mechanism may include an objective, a prism, or another optical device that forms part of an optical train of an imaging mechanism, a sensor for measuring a distance to the target surface, and a mechanism for modifying the depth of focus of the objective, prism or other optical device. Data from the sensor may be used to create a predictive model of the target surface. Data from the sensor is also used to fit or correlate the generated model to an exemplary target. Data from the correlated model is used to drive the mechanism for modifying the depth of focus of the objective, prism, or other optical device to maintain the surface of the exemplary target in focus.

21 Claims, 5 Drawing Sheets

U.S. PATENT DOCUMENTS

| | | |
|---|---|---|
| 6,107,637 A | 8/2000 | Watanabe et al. |
| 6,172,365 B1 | 1/2001 | Hiroi et al. |
| 6,208,407 B1 | 3/2001 | Loopstra |
| 6,211,745 B1 | 4/2001 | Mucke et al. |
| 6,292,265 B1 | 9/2001 | Finarov et al. |
| 6,324,298 B1 | 11/2001 | O'Dell et al. |
| 6,597,006 B1 | 7/2003 | McCord et al. |
| 6,611,344 B1 | 8/2003 | Chuang et al. |
| 6,674,510 B1 | 1/2004 | Jasper et al. |
| 6,674,574 B1 * | 1/2004 | Aono ................. 359/383 |
| 6,801,326 B2 | 10/2004 | Finarov et al. |
| 6,812,446 B2 * | 11/2004 | Kreh ................. 250/201.3 |
| 6,864,474 B2 * | 3/2005 | Misawa ............. 250/201.4 |
| 6,875,972 B2 * | 4/2005 | Kreh ................. 250/201.3 |
| 6,876,438 B2 | 4/2005 | Tokita |
| 6,884,980 B2 * | 4/2005 | Spink ................ 250/201.3 |
| 6,974,938 B1 * | 12/2005 | Leblans et al. .... 250/201.3 |
| 7,015,445 B2 | 3/2006 | Bishop |
| 2002/0100872 A1 | 8/2002 | Hiroi et al. |
| 2002/0109071 A1 * | 8/2002 | Spink ................ 250/201.4 |
| 2003/0053676 A1 | 3/2003 | Shimoda et al. |
| 2003/0164440 A1 * | 9/2003 | Czarnetzki et al. ... 250/201.3 |
| 2004/0021877 A1 | 2/2004 | Clark |
| 2004/0031779 A1 | 2/2004 | Cahill et al. |
| 2004/0051673 A1 | 3/2004 | Oberski et al. |
| 2004/0080742 A1 | 4/2004 | Mizuo et al. |
| 2004/0130691 A1 | 7/2004 | Boonman et al. |
| 2006/0201240 A1 | 9/2006 | Morinaga |

\* cited by examiner

DYNAMIC FOCUSING METHOD AND APPARATUS

CROSS-REFERENCE TO RELATED APPLICATION

This application is a divisional of U.S. Ser. No. 11/179,047, filed Jul. 11, 2005 now U.S. Pat. No. 7,196,300, which claims priority to and the benefit of Provisional Patent Application Nos. 60/587,302, 60/587,216 and 60/587,570, all filed on Jul. 12, 2004, and is a continuation-in-part of U.S. patent application Ser. No. 10/622,848, filed on Jul. 18, 2003 now U.S. Pat. No. 7,170,075, the teachings of each of which are incorporated herein by reference in their entireties.

TECHNICAL FIELD OF THE INVENTION

The present invention relates generally to methods and mechanism for maintaining focus in an optical system.

BACKGROUND OF THE INVENTION

Wafer inspection systems generally use a vacuum chuck to hold a silicon wafer during inspection. The advantage of this method is that the wafer surface can be as flat as the machined surface of the vacuum chuck. Systems in which a wafer rests on a vacuum chuck or other flat surface are not particularly flexible and require complex and expensive staging mechanisms to move the surface on which the wafer rests and/or the imaging system used to capture images of the wafer. Other wafer inspection systems float silicon wafers on a cushion of air. This type of system suffers from positioning errors in that there is inherent variation in the position a wafer that is not positively gripped. What is more, the contact between the edge of a wafer and a rotary positioning mechanism often gives rise to small chips and other defects at the edge that may contaminate the entire wafer, especially as the air cushion provides a means for distributing contaminants over the surface of the wafer. Yet other systems use robotic devices or manipulators that rotate the wafer about multiple, orthogonal axes to gain access to the backside of a wafer. But because wafers do flex somewhat as a result of such manipulation, it is possible to damage the wafer itself and/or the microelectronic structures formed thereon.

One solution to the problems faced by the inspection systems described above is to grip a silicon wafer by its edges and to rotate the wafer about a vertical axis such that an imaging mechanism may capture images of the entire backside of the wafer. This method limits the stresses applied to a wafer and avoids damage thereto. However, in some instances and because gripping a wafer only at its edges does not support the entire wafer surface, it is possible for a wafer to sag or deform under the influence of gravity. Where relatively low magnification optics are used to capture images of the wafer, the depth of focus of these optics will generally be large enough to ensure that the surface of the wafer will remain in focus during inspection. But where relatively higher magnification optics are used, it is possible that a significant portion of the wafer surface may at some point fall outside the depth of focus of the inspection optics, thereby resulting in poor performance of the system.

Accordingly, there is need for a method and apparatus for characterizing the sag or deformation of an edge supported wafer and using this characterization to ensure that the optics of an imaging system remain focused on the surface of a wafer during the imaging of the wafer surface.

DETAILED DESCRIPTION

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

Figure 1:
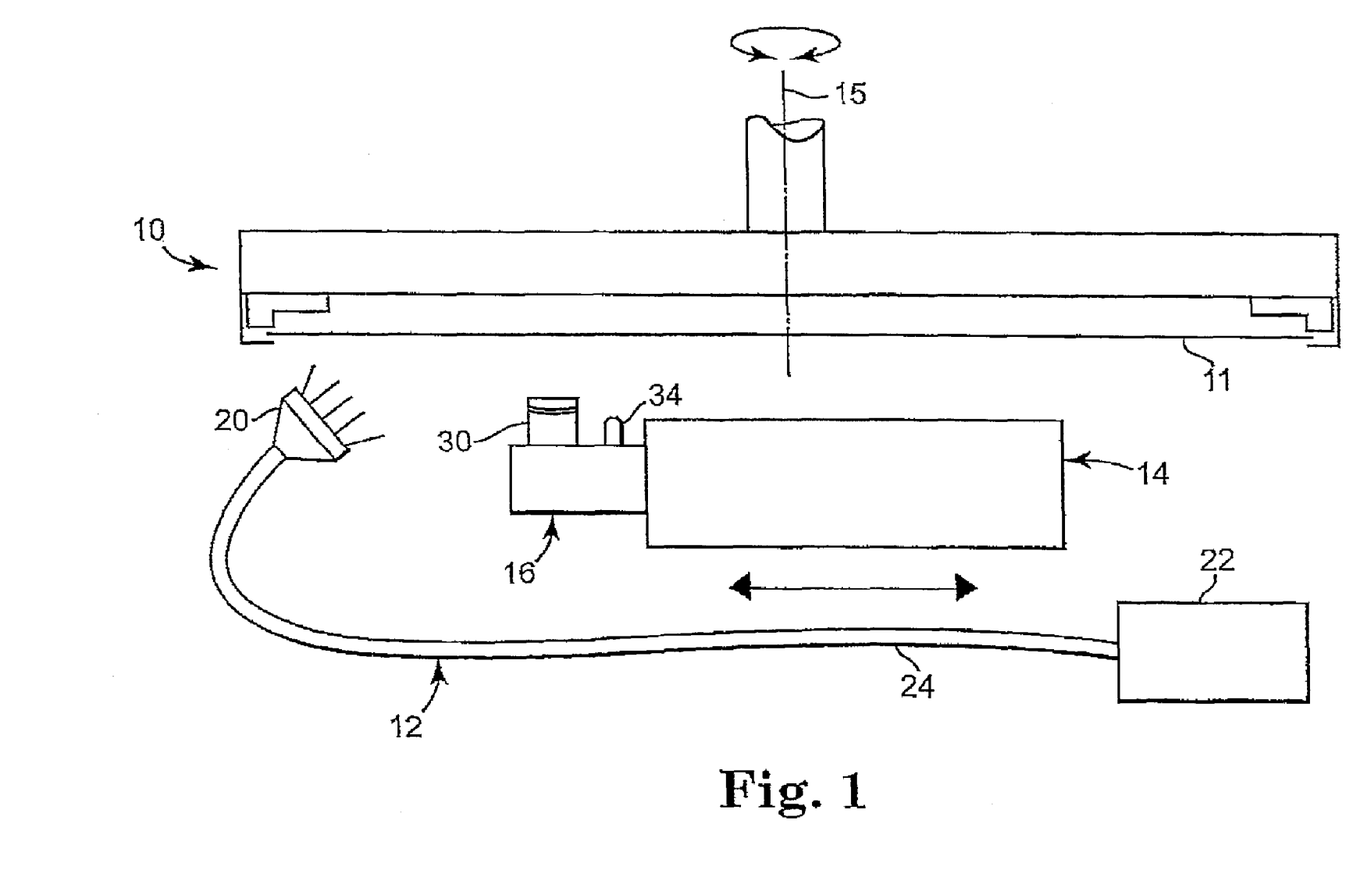
FIG. 1 is a schematic side view of a mechanism for inspecting a substrate that includes a mechanism for dynamically focusing an imaging mechanism on the substrate as the substrate moves relative to the imaging mechanism.

Turning first to FIG. 1, a mechanism 10 for holding a substrate 11 such as a wafer of the type used in the manufacture of semiconductor and micro-electromechanical (MEMS) devices is pictured in relation to an illumination mechanism 12 and an imagining mechanism 14. The holding mechanism 10 securely grips a substrate 11 at its edges such that there is substantially no relative motion between the mechanism 10 and the substrate 11. The mechanism 10 is further arranged such that a surface of the substrate 11, in the embodiment illustrated in FIG. 1 the bottom surface of the substrate 11, is substantially entirely accessible to the imaging mechanism 14 such that substantially the entire under surface of the substrate 11 may be imaged.

Figure 2:
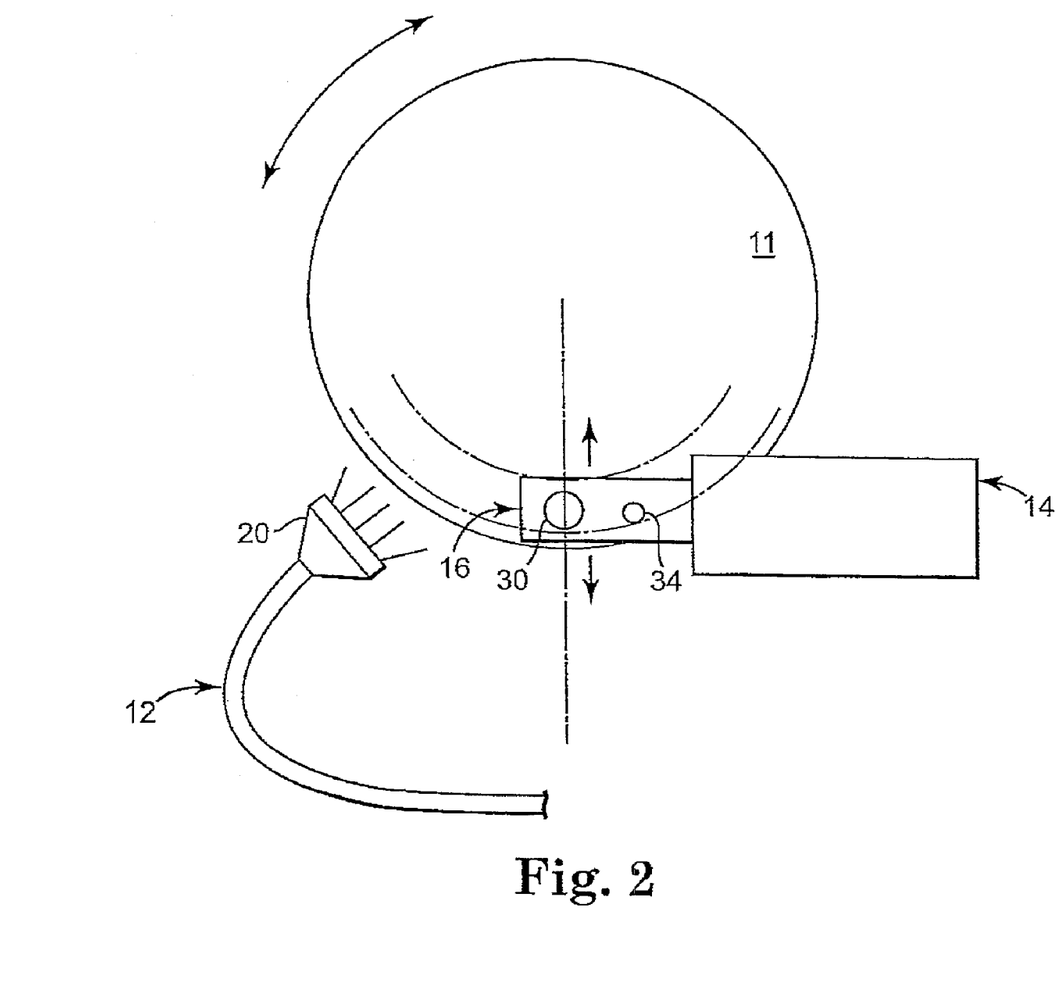
FIG. 2 is a schematic top view of an embodiment of the mechanism for inspecting a substrate wherein the imagining mechanism moves relative to the substrate during inspection.

The holding mechanism 10 is adapted to move the substrate 11 with respect to the imaging mechanism 14. In the embodiment of FIG. 1, the holding mechanism 10 rotates the substrate 11 about an axis as indicated by arrow 15. Note that in other embodiments, the holding mechanism 11 may be further adapted to move the substrate 11 with respect to the imaging mechanism 14 in a linear, curvilinear, and/or discontinuous manner. What is more, as seen in FIG. 2, in some embodiments, the imaging mechanism 14 may be adapted to move with respect to the substrate 11, which may simultaneously move as described hereinabove. In one embodiment, the imaging mechanism 14 works with the holding mechanism 10 to permit the imaging mechanism 14 to capture images of substantially the entire surface of the substrate 11. As will be appreciated, as the substrate 11 is rotated with respect to the imaging mechanism 14, the imaging mechanism 14 is operated to capture successive images around a ring R of the substrate 11. Once the entire ring R is imaged, the imaging mechanism 14 will move radially with respect to the substrate 11 to capture images of another ring R of the substrate 11. In this manner, images of substantially an entire surface of the substrate 11 may be captured. Note that in some instances and depending on the orientation of the holding mechanism 10 and the imaging mechanism 14, the surface of the substrate 11 being imaged may be the upper or lower surface of the substrate 11.

Figure 4A:
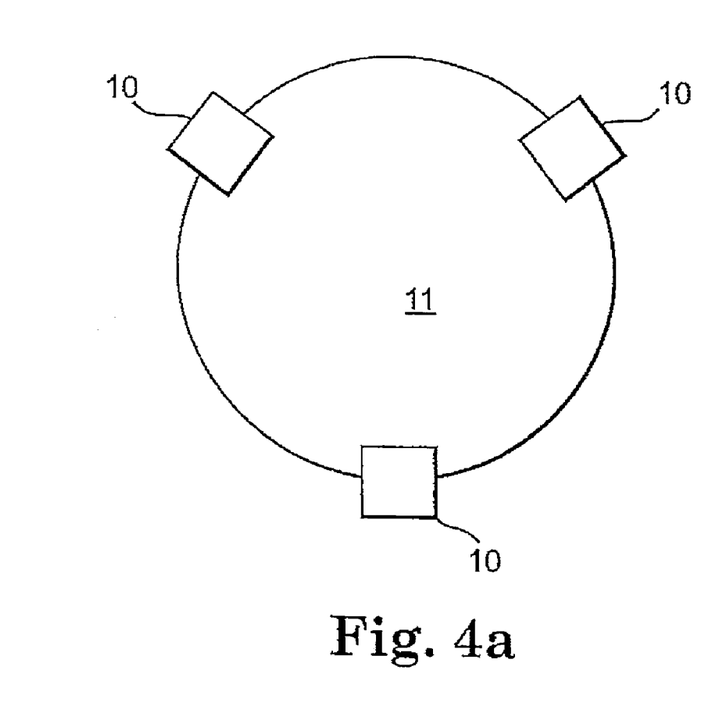
FIGS. 4a and 4b are examples of boundary conditions for substrates secured for inspection.
Figure 4B:
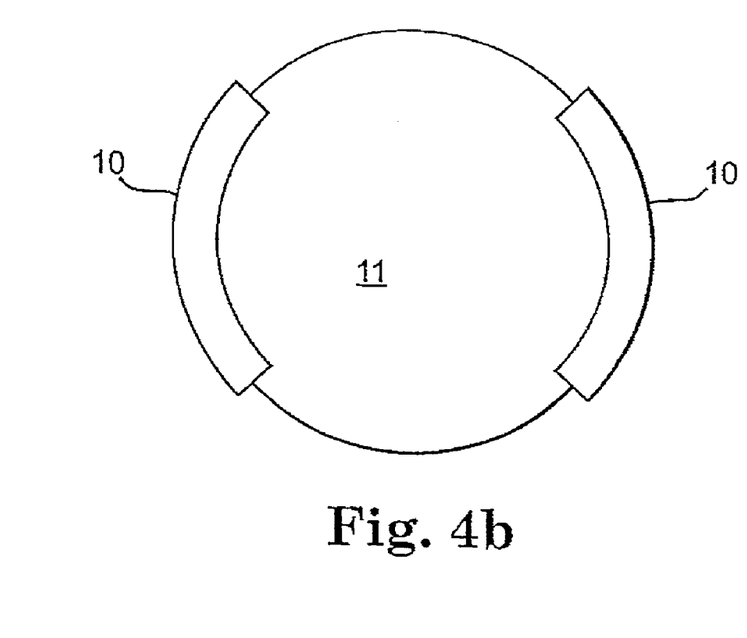

Holding mechanism 10 may grip a substrate 11 in many different arrangements. In FIG. 4a, the peripheral edge of the substrate 11 is gripped by the holding mechanism in three locations spaced approximately 120° apart. In FIG. 4b, another embodiment of the holding mechanism 10 grips relatively large portions of the peripheral edge of the substrate 11 at two locations. Other arrangements area contemplated.

The imaging mechanism 14 may be moved radially with respect to the holding mechanism 10 by mounting the imaging mechanism 14 on a single axis stage (not shown) of a type known in the art. Where, as in some embodiments, the holding mechanism 10 does not move the substrate, the imagining mechanism 14 may be mounted on an XY stage such that a focusing mechanism 16 of the optical train of the imaging mechanism 14 may be addressed to substantially an entire surface of the substrate 11 along a continuous or discontinuous serpentine path.

Illumination mechanism 12 illuminates the substrate 11 such that imaging mechanism 14 may capture images of the substrate 11. In one embodiment the illumination mechanism 12 is a darkfield illuminator adapted to emit light onto the substrate at a relatively low angle. As seen in FIG. 1, the illuminating mechanism 12 includes an emitter 20 that is coupled to a light source 22 by a light guide 24, which may be a multi-strand fiber optic cable, a solid light pipe, or a liquid light guide. It is to be understood that a darkfield embodiment of the illumination mechanism 12 may take any useful form capable of emitting sufficient light onto the surface of the substrate 11. In some instances, the illuminating mechanism 12 may be a one or more lasers (not shown) arranged to emit coherent light onto the surface of the substrate 11 or even a ring light (not shown). The imaging mechanism 14 may itself be provided with a brightfield illuminator incorporated into the optic train of the imaging mechanism 14 in a manner known to those skilled in the art.

Figure 3:
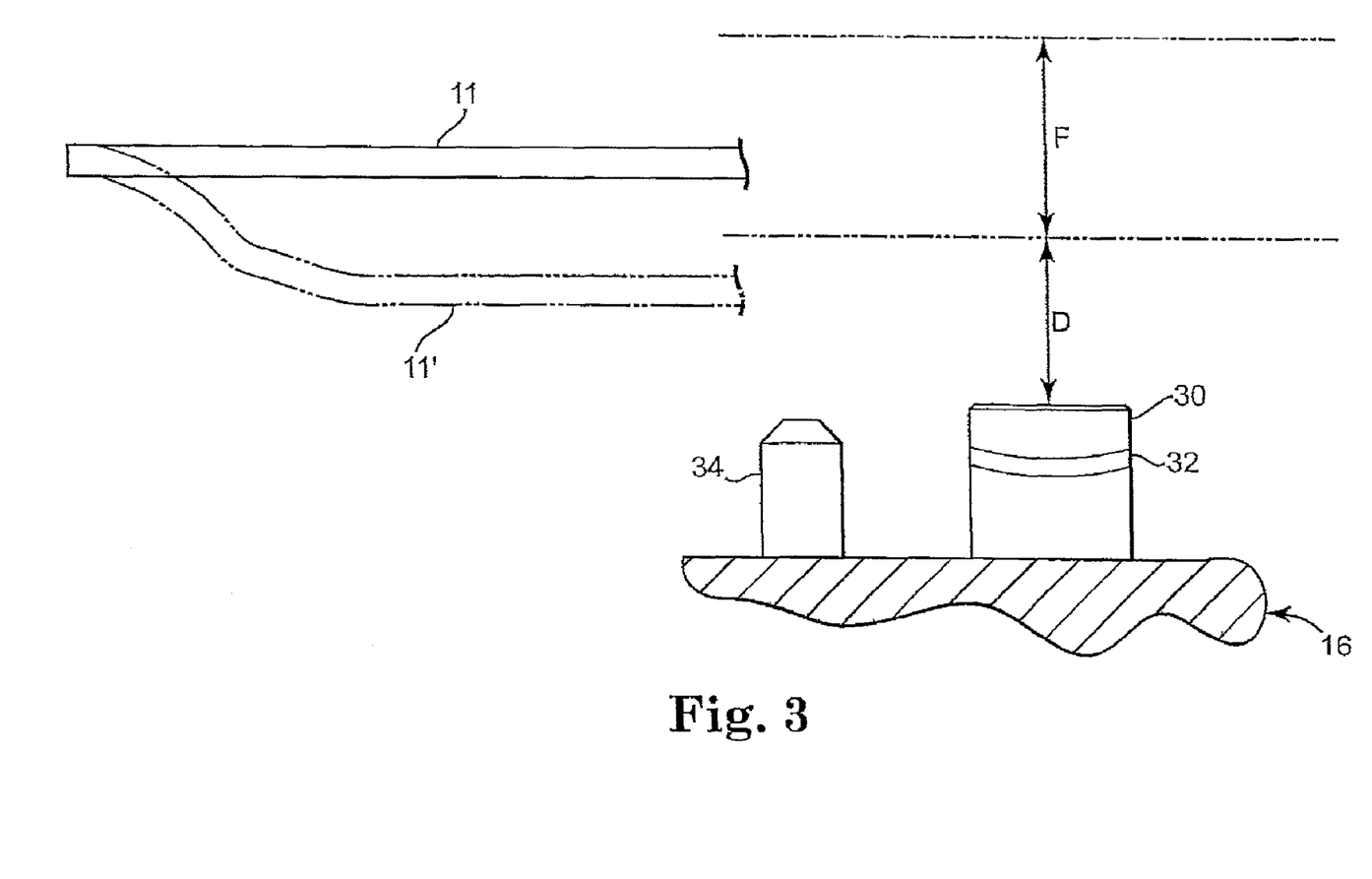
FIG. 3 is a close up schematic view of a substrate having a variable geometry wherein an imaging mechanism is positioned to capture images of the substrate for inspection.

FIG. 3 illustrates schematically an objective 30 of one embodiment of imaging mechanism 14. Each objective 30 or other optical device used in the same manner as is objective 30 has associated therewith a depth of focus F. As used herein, the term "depth of focus" refers to a range of distances over which the objective 30 is able to resolve images to an acceptable level of clarity. As seen in the Figure, the depth of focus F is generally broad enough to span the entire depth of a substrate 11, such that the entire surface of the substrate 11 facing the objective 30 is in focus at all times as the substrate 11 moves relative to the objective 30. But, as described above, where a substrate is secured only at its edges, it is possible for the substrate 11 to behave, at least to a degree, as an elastic membrane and to consequently deform. An exaggerated deformed substrate 11' is shown in FIG. 3. While the deformed substrate's shape is exaggerated, it is to be understood that in some instances, the substrate 11' may deform to a degree that is outside of the depth of focus F of the objective 30. Where the substrate 11' does fall outside of the depth of focus F of the objective, a focusing mechanism 32 may be activated to change the focal distance D of the objective 30 and moving the depth of focus F of the objective 30 to a position that encompasses the substrate 11, thereby bringing the substrate 11' into focus.

Where a substrate 11 is moved relative to an objective 30 of a imaging mechanism 14 it will often be necessary to dynamically modify the focal distance D of the objective 30 to maintain the substrate 11 within the depth of focus F of the objective 30 as the movement of the substrate 11 past the objective 30 in a plane that is generally not co-incident with the focal axis of the objective may take portions of the substrate 11 out of the depth of focus F of the objective. In some instances it may be possible to measure the distance between the substrate 11 and the objective 30, or rather some arbitrary position on the imaging mechanism 14, "on the fly" that is, as the substrate 11 moves using a sensor 34. Such a sensor, in one embodiment a capacitative sensor, senses a calibrated distance between the substrate 11 and the imaging mechanism 14 and controls the focusing mechanism 32 using this distance data to ensure that the substrate 11 remains within the depth of focus F of the objective 30 at all times. However, such direct control of the focusing mechanism 32 can be relatively slow as the response times of many prior art focusing mechanisms 32 lag significantly behind the measurement rate of commonly used sensors 34.

In another embodiment, the predicted, deformed shape of a substrate 11 is modeled to provide data to the focusing mechanism 32 at a faster rate than is possible using a sensor 34 as data regarding the shape of the substrate 11 is already known and/or recorded. However, because of variations in the properties of even similarly patterned exemplary substrates 11, the exact shape of a substrate is difficult to know. Accordingly, classically or empirically derived models representing the deformed shape of a substrate 11 may be modified or correlated using distance data captured by a sensor 34 as described above such that the model(s) are in accord with the actual shape of the substrate to within an acceptable tolerance. In some embodiments, the tolerance referred to is related to the depth of focus F of the objective 30, i.e. discrepancies between the model and the exemplary substrate 11 to be inspected are considered acceptable so long as the data provided by the model, modified or unmodified, permits the focusing mechanism 32 to maintain the surface of the substrate within the depth of focus F of the objective 30.

In one embodiment, a method of modeling the shape of a substrate 11 begins with determining the boundary and loading conditions of the substrate as illustrated in FIGS. 4a and 4b. Using the boundary and loading conditions, a model of the ultimate shape of the substrate 11 may be derived using known classical structural analysis techniques. Once a suitable classical model has been derived, this model is fitted to subsequent, similarly situated substrates 11 using a number of measurements of the surface of the substrate 11 taken at predetermined locations using a sensor such as sensor 34. Data derived from the fitted model is then used to drive the focusing mechanism 32 to ensure that the surface of the substrate 11 remains in focus.

In another embodiment, a method of modeling the shape of a substrate 11 begins with inputting information concerning the geometry of the substrate 11 and any structures formed thereon and the nature of materials from which they are made, as well as information concerning the boundary and loading conditions of the substrate, into a computer running a finite element analysis program. The finite element analysis program is then operated to generate a model of the substrate 11 that provides data that may be used to drive a focusing mechanism 32 to ensure that the surface of the substrate 11 remains in focus for imaging. The finite element analysis generated model may be used as-is, or may be further fitted to an actual substrate's shape using a number of measurements taken with a sensor, such as sensor 34, at predetermined positions as described above.

In yet another embodiment, a method of ensuring that an imaging mechanism 14 remains focused on a substrate 11 begins with measuring the distance between a substrate 11 and a sensor 34 at a predetermined number of positions on the substrate 11. Using these measurements, a model of the surface of the substrate 11 is created using a suitable interpolation or 'fitting' algorithm. By way of example only, some suitable algorithms for creating a model of the shape of substrate 11 include, but are not limited to: natural neighbor interpolation, surface patches, quadratic surfaces, polynomial interpolation, spline interpolation and Delauney triangulation. Once a model has been created for a given substrate 11 and for given loading and boundary conditions, this model is used to provide data to the focusing mechanism 32 to ensure that the surface of the substrate 11 stays within the depth of focus F of the objective 30 at substantially all times. To ensure that the model is fitted to a particular substrate 11 that is to be inspected, sometimes referred to as a target, target surface and/or exemplary substrate, a set of fitting measurements of the target are taken. These fitting measurements are used to fit the model to the target substrate by determining whether there are discrepancies between the model and the target substrate and by generating correction factors that are used to modify the model such that any identified discrepancies are minimized. By way of example only, some discrepancies that are corrected for may include, but are not limited to: phase misalignment (where the model is rotated with respect to the target substrate), lack of planarity (where the model is out of planar alignment with the target substrate), and offset errors in which the model is offset from the target substrate in a direction or to a degree that negatively affects the ability of the focusing mechanism's ability to maintain the target substrate 11 within the depth of focus F of the objective 30. In some embodiments, discrepancies that do not cause the target substrate to move out of the depth of focus F of the objective 30 will not be corrected for. In other embodiments, all discrepancies are corrected.

Figure 5:
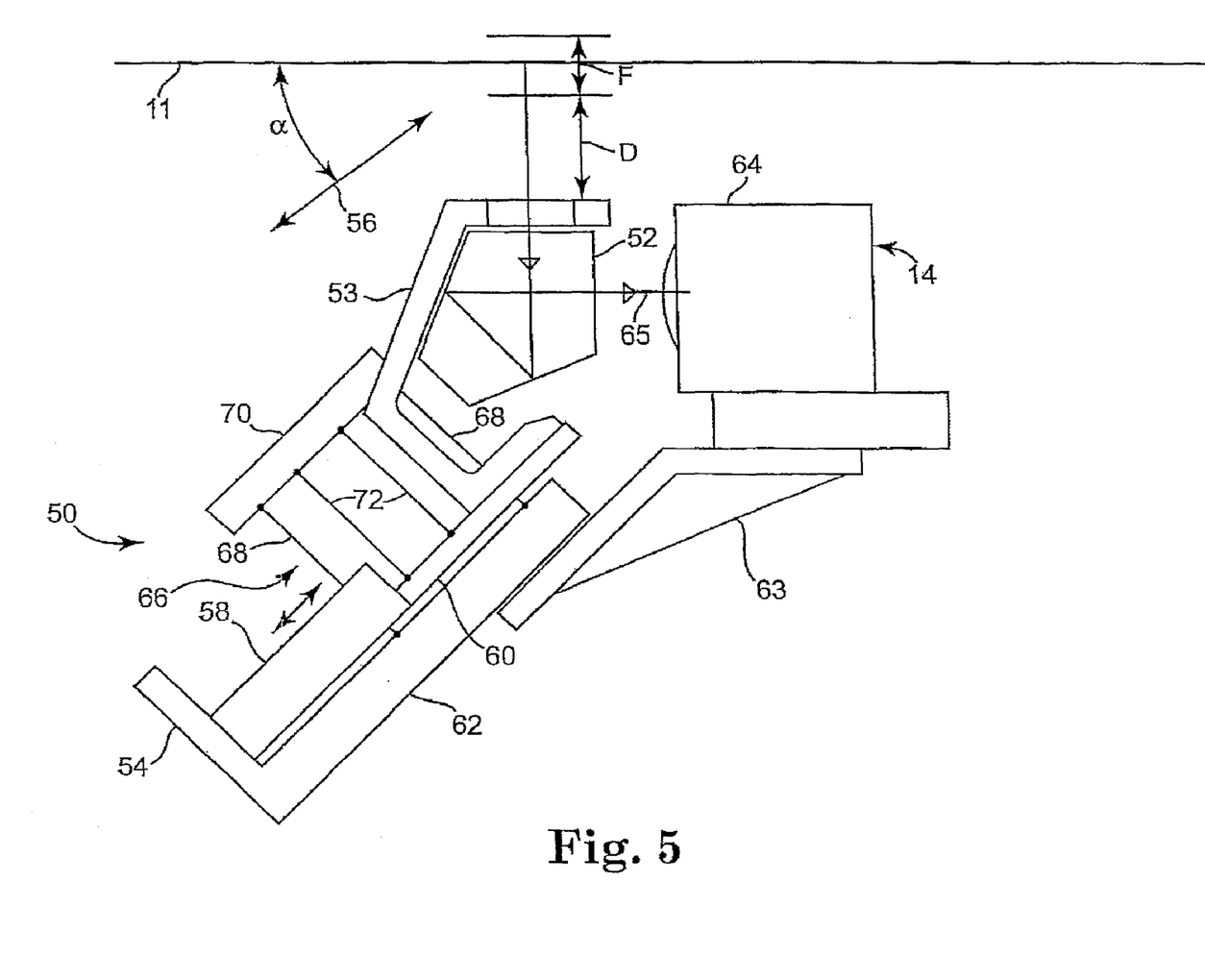
FIG. 5 is a schematic view of a focusing mechanism for maintaining the surface of a substrate within a field of focus of an imaging mechanism.

FIG. 5 illustrates schematically another embodiment of a device for focusing an optical train on a surface of a target substrate 11, the mechanism being identified in FIG. 5 by reference numeral 50. Focusing device 50 includes a focusing prism 52 that is mounted on an armature 54 that permits the movement of the prism 52 toward and away from the substrate 11, thereby maintaining the substrate 11 within the depth of focus F of the prism 52. In one embodiment, armature 54 includes a compound parallel linkage 66 that moves the focusing prism 52 toward and away from the target substrate 11 along a path shown by arrow 56. Note that arrow 56 is at an angle α with respect to the target substrate 11. Moving the focusing prism 52 along in the direction indicated means that the prism 52 changes the distance D between the focusing prism 52 and the substrate by an amount equal to the magnitude of translation along path 56 multiplied by the sine of angle α. In one embodiment, the distance D is modified from a starting point by ±0.5 mm.

The prism 52 is moved along path 56 by a linearly extensible actuator 58 of any useful type. By way of example and without limiting the nature or type of actuator that may be used, the actuator 58 may be a solenoid or a piezoelectric actuator. The actuator 58 is coupled between a stage 60 and a base 62 of the device 50. The prism 52 is coupled to a holder 53 that is secured to the stage 60. Base 62 of the device 50 is, in one embodiment, coupled directly to an imaging device 64 of a suitable type by means of a bracket 63. As seen in FIG. 5, the stage 60 is coupled to the base 62 by a compound parallel linkage 66 in which at least one pair of first arms 68 are coupled between the base 62 and a bridge 70. At least one pair of second arms 72 are coupled between the bridge 70 and the stage 60. Because the arms of the at least one pair of first arms 68 are all substantially the same length, the bridge 70 is translated in a shallow arcuate path with respect to the base 62, remaining substantially parallel thereto at all times. Similarly, because the at least one pair of second arms 72 are of equal or substantially equal length, the stage 60 is translated along a shallow arcuate path with respect to the bridge 70, remaining substantially parallel thereto at all times. And, because the arcuate paths of the bridge 70 and the stage 60 are substantially mirror images of one another, the resulting translation of the prism 52 along path 56 is substantially linear. Note that in some embodiments, a simply parallel linkage may be used to translate the prism 52 along path 56 in an arcuate fashion.

In one embodiment, the joints between the pairs of first and second arms and the base 62, bridge 70 and stage 60 are all solid spring joints in which arms, base, bridge, and stage are all formed in a single contiguous structure, the joints being formed by thin, flexible members that allow for elastic deformation and translation between the respective portions of the contiguous structure. Note that the size and configuration of such solid joints are such that the stresses and strains placed on the solid joints between the arms and the base, bridge, and stage are relatively low and in one embodiment are such that deformation of the joints is substantially elastic and results in substantially no plastic deformation or cracking of the material from which the armature is fashioned. In another embodiment, the pairs of first and second arms are joined to the base, bridge and stage using standard pin joints.

As can be appreciated from FIG. 5, prism 52 receives light from the surface of the target 11 and transmits that light to the imaging mechanism 64 as represented schematically by ray 65. In one embodiment the prism 52 is a penta-prism, though other prisms, lenses, or combinations thereof may be substituted therefore. In one embodiment, the prism 52 provides a magnification or gain with respect to the images transmitted therethrough of approximately the square root of 2, though it is to be understood that the gain provided by the prism 52 or its optical equivalent will vary depending on the exact geometry and optical characteristics of the prism and its equivalents.

Because the combined inertial mass and mechanical resistance to movement of the prism 52, its holder 53, and the armature 54 to which they are coupled are relatively low, the actuator 58 is able to quickly and smoothly modify the focal distance D. This ensures that the surface of the substrate 11 remains in focus substantially all the time and allows for more rapid operation of an inspection system incorporating the focusing mechanism 50 as there is a direct correlation between the rate at which the substrate may be moved relative to the imaging mechanism 14 and the rate at which the focal distance D may be modified. What is more, the use of a focusing mechanism 50 in an inspection system permits the inspection system to operate at higher speeds while using only a sensor 34 to determine variations in surface geometry of a substrate 11 being inspected.

CONCLUSION

While various examples were provided above, the present invention is not limited to the specifics of the examples. The present invention embodies, among other things, a method of correlating a model of a structure with one or more actual examples of the structure and a method for correcting for discrepancies between the model and the actual structure. The present invention also provides a mechanism that provides data for correlating a model of a structure with an actual example of the structure and embodiments of a dynamic focusing mechanism that uses data from the model and its correlation with an exemplar to maintain a surface of the exemplar within a depth of focus of an optical train.

Although specific embodiments of the present invention have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. An imaging mechanism for capturing images of a moving surface having a variable geometry comprising:
   a camera for capturing images;
   a focusing assembly that defines an optical path between the moving surface and the camera, the focusing assembly including a prism adapted for substantially parallel movement toward and away from the moving surface, the distance between the prism and the moving surface being related to the depth of focus of the focusing assembly; and
   an illuminator for illuminating the moving surface.

2. The imaging mechanism for capturing images of a moving surface having a variable geometry of claim 1 wherein the camera is one of an area scan camera and a line scan camera.

3. The imaging mechanism for capturing images of a moving surface having a variable geometry of claim 1 wherein the imaging mechanism is mounted on a moveable stage for movement relative to the moving surface.

4. The imaging mechanism for capturing images of a moving surface having a variable geometry of claim 3 wherein the focusing assembly further comprises:
   a parallel linkage having a base and a plurality of arms, the base being coupled to the moveable stage and the arms being coupled to the base for rotation relative thereto, the prism of the focusing assembly being coupled to the arms of the parallel linkage for movement toward and away from the moving surface, the prism remaining substantially parallel to a plane defined by the moving surface.

5. The imaging mechanism for capturing images of a moving surface having a variable geometry of claim 4 further comprising an actuator coupled between the base of the parallel linkage and the prism for moving the prism toward and away from the moving surface.

6. The imaging mechanism for capturing images of a moving surface having a variable geometry of claim 5 wherein the actuator is chosen from a group consisting of a solenoid and a piezoelectric device.

7. The imaging mechanism for capturing images of a moving surface having a variable geometry of claim 3 wherein the moving surface rotates with respect to the imaging mechanism.

8. The imaging mechanism for capturing images of a moving surface having a variable geometry of claim 7 wherein the moveable stage moves the imaging mechanism in a radial direction with respect to the moving surface so as to address substantially the entire moving surface.

9. The imaging mechanism for capturing images of a moving surface having a variable geometry of claim 8 wherein the imaging mechanism is controlled to capture a plurality of images of a plurality of sectors of the moving surface.

10. The imaging mechanism for capturing images of a moving surface having a variable geometry of claim 7 wherein the imaging mechanism further comprises a line scan camera and wherein the moveable stage is adapted to address the line scan camera to a plurality of annuli of the moving surface.

11. The imaging mechanism for capturing images of a moving surface having a variable geometry of claim 1 wherein the imaging mechanism comprises a line scan camera having a width greater than a radius of the moving surface.

12. The imaging mechanism for capturing images of a moving surface having a variable geometry of claim 1 wherein the moving surface is a silicon wafer.

13. The imaging mechanism for capturing images of a moving surface having a variable geometry of claim 12 wherein the moving surface is the bottom side of a silicon wafer.

14. The imaging mechanism for capturing images of a moving surface having a variable geometry of claim 1 wherein the moving surface rotates with respect to the imaging mechanism.

15. The imaging mechanism for capturing images of a moving surface having a variable geometry of claim 1 wherein the illuminator is one of a brightfield illuminator and a darkfield illuminator.

16. The imaging mechanism for capturing images of a moving surface having a variable geometry of claim 1 wherein the illuminator comprises a source and an emitter that is located remotely from the source, the source and the emitter being coupled by a light guide assembly.

17. The imaging mechanism for capturing images of a moving surface having a variable geometry of claim 1 wherein the illuminator strobes at a rate based on the velocity of the moving surface relative to the imaging mechanism.

18. The imaging mechanism for capturing images of a moving surface having a variable geometry of claim 1 wherein the focusing assembly further comprises:
   a parallel linkage having a base and a plurality of arms, the arms being coupled to the base for rotation relative thereto, the prism of the focusing assembly being coupled to the arms of the parallel linkage for movement toward and away from the moving surface, the prism remaining substantially parallel to a plane defined by the moving surface.

19. The imaging mechanism for capturing images of a moving surface having a variable geometry of claim 18 further comprising an actuator coupled between the base of the parallel linkage and the prism for moving the prism toward and away from the moving surface.

20. The imaging mechanism for capturing images of a moving surface having a variable geometry of claim 19 wherein the actuator is chosen from a group consisting of a solenoid and a piezoelectric device.

21. An imaging mechanism for capturing images of a moving surface having a variable geometry comprising:

a camera for capturing images;

a focusing assembly that defines an optical path between the moving surface and the camera, the focusing assembly including a prism adapted for substantially parallel movement toward and away from the moving surface, the distance between the prism and the moving surface being related to the depth of focus of the focusing assembly;

an illuminator for illuminating the moving surface; and, a sensor for determining a distance between the moving surface and the focusing assembly, the distance data captured by the sensor being used to drive the focusing assembly to maintain the moving surface within the depth of focus thereof.

* * * * *